United States Patent
Goodman et al.

[11] Patent Number: 5,955,670
[45] Date of Patent: Sep. 21, 1999

[54] ULTRASONIC LEAK DETECTING APPARATUS

[75] Inventors: Mark Goodman, Courtlandt Manor, N.Y.; John R. Zeno, deceased, late of New York, N.Y.; Linda Mabbs, executrix, Alexandria, Va.

[73] Assignee: UE Systems, Inc, Elmsford, N.Y.

[21] Appl. No.: 08/749,910

[22] Filed: Nov. 15, 1996

[51] Int. Cl.$^6$ .......................... G01H 17/00; G01N 29/12; G01N 29/14

[52] U.S. Cl. .......................... 73/592; 73/593; 73/40.5 A; 340/605

[58] Field of Search ................................ 73/40.5 A, 592, 73/593; 367/135; 340/605; 364/507

[56] References Cited

U.S. PATENT DOCUMENTS

| | | | |
|---|---|---|---|
| 4,287,581 | 9/1981 | Neale, Sr. ................................ | 367/135 |
| 4,416,145 | 11/1983 | Goodman et al. .................... | 73/40.5 A |
| 4,635,042 | 1/1987 | Andrews ................................. | 340/605 |
| 4,785,659 | 11/1988 | Rose et al. ............................ | 73/40.5 A |
| 4,800,512 | 1/1989 | Busch .................................. | 364/551.01 |
| 4,823,600 | 4/1989 | Biegel et al. ............................. | 73/592 |
| 4,987,769 | 1/1991 | Peacock et al. ........................... | 73/49.7 |
| 5,089,997 | 2/1992 | Pecukonis ................................ | 367/135 |
| 5,140,858 | 8/1992 | Nishimoto et al. ....................... | 73/587 |
| 5,350,040 | 9/1994 | Gribble ................................ | 184/105.2 |
| 5,432,755 | 7/1995 | Komninos ................................ | 367/135 |

OTHER PUBLICATIONS
PCT Search Report dated Mar. 9, 1998 for Application PCT/US97/22079.

Primary Examiner—Hezron E. Williams
Assistant Examiner—Rose M. Miller
Attorney, Agent, or Firm—Darby & Darby

[57] ABSTRACT

An ultrasonic leak detector with a wide dynamic bandwidth and repeatable fixed attenuation reference points includes a transducer which receives ultrasonic energy and converts it into an electrical output signal related in intensity and frequency to the received ultrasonic energy. A high gain charge preamplifier is connected to the transducer and generates an amplified version of the transducer's electrical output signal. The amplified signal is then passed through a multi-level logarithmic attenuator having at least one fixed attenuation reference point to create an attenuated version of the detected and amplified ultrasonic signal. The output of the logarithmic attenuator is connected to a frequency shift circuit which converts the ultrasonic frequency signal into an audio frequency signal related in magnitude and frequency to the attenuated signal. The audio frequency signal is then amplified by an audio amplifier and used to drive a signal level indicator which provides an indication of the magnitude of the amplified output signal. The detector may be used with a lubrication tool to determine the amount of lubrication applied to a sealed mechanical device, such as a bearing, by detecting the decrease in received ultrasonic energy as the lubrication reaches the device. The detector may also be used to detect the increase in ultrasonic energy associated with pending mechanical failure.

38 Claims, 5 Drawing Sheets

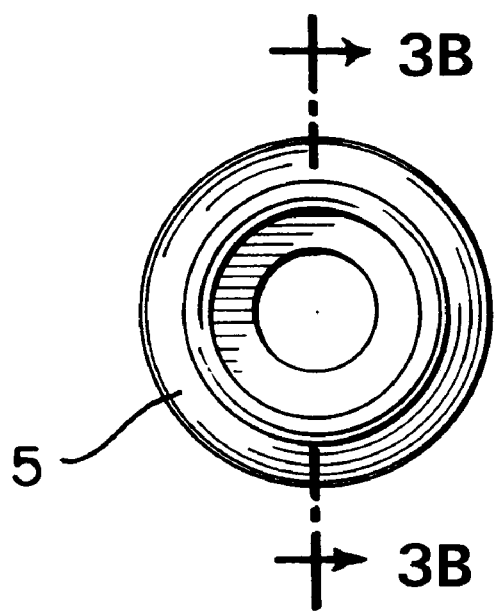
FIG. 3A
FIG. 3B
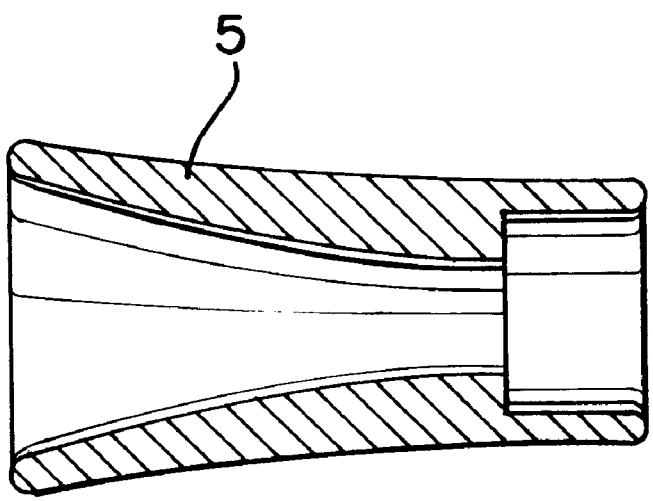

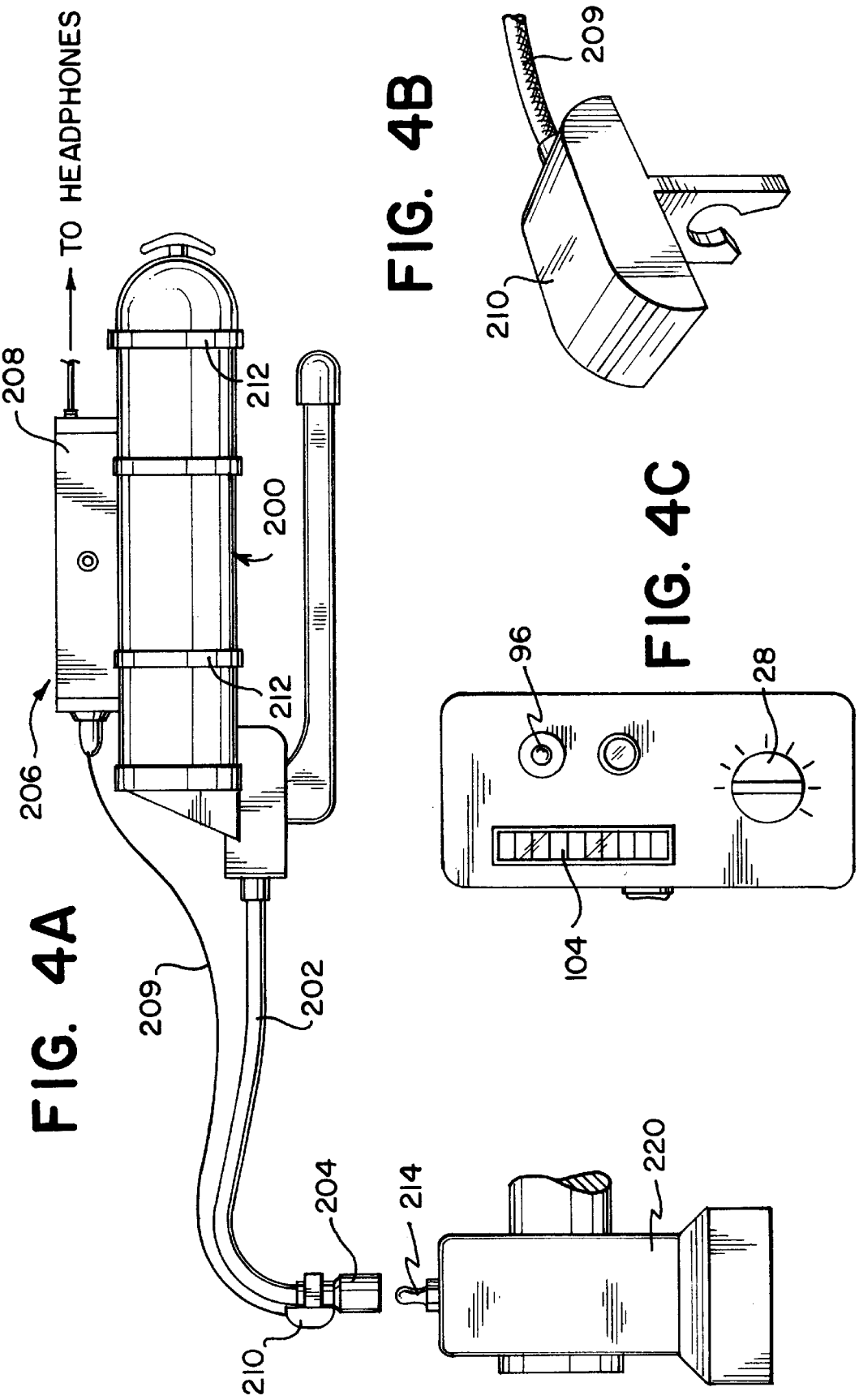

ULTRASONIC LEAK DETECTING APPARATUS

BACKGROUND OF THE INVENTION

1. Field of the Invention

The invention pertains to an ultrasonic detector and more specifically to a light weight, battery-operated, precision instrument for detecting ultrasonic sound or vibrations, which is useful in detecting leaks and malfunctions.

2. Prior Art

It is well known that ultrasonic generators and detectors can be used to locate leaks or defects, e.g. in pipes. Such a system is shown in U.S. Pat. No. 3,978,915 to Harris. In that arrangement, ultrasonic generators are positioned in a chamber through which the pipes pass. At the ends of these pipes, exterior to the chamber, ultrasonic detectors are located. At the point where a leak occurs in the pipe or the pipe wall is thin, the ultrasonic energy will enter the pipe from the chamber and travel to the end of the pipe where the detector is located. The detector will receive an ultrasonic signal at the end of the pipe indicating the existence of the leak or weak spot in the pipe.

Ultrasonic sensors have also been used to detect ultrasonic energy generated by friction within mechanical devices as disclosed in U.S. Pat. No. Re. 33,977 to Goodman, et al. The greater the amount of friction, the greater the intensity of the generated ultrasonic energy. Applying a lubricant to the device reduces friction and consequently the intensity of the generated ultrasound drops. Measuring ultrasonic energy thus provides a way to determine when lubrication has reached the friction generating surfaces. Additionally, faulty devices such as bearings generate a higher level of ultrasonic energy than do good bearings, and thus this condition can also be detected. However, conventional means require two people to perform this procedure—one person to apply the lubricant to the device, and one person to operate the ultrasonic detector.

Since ultrasonic energy used for these purposes is generally in the range of 40 kHz, it is too high in frequency to be heard by a human being. Thus, means are typically provided for heterodyning or frequency shifting the detected signal into the audio range, and various schemes are available for doing this.

By locating an ultrasonic generator in a closed chamber, a standing wave pattern with peaks and nodes is established. If a node occurs at the position of a leak or weak spot, no ultrasonic energy will escape and the defect will not be detected. One method of addressing this problem is disclosed in U.S. Pat. No. Re. 33,977 to Goodman, et al. Goodman teaches varying the frequency of the applied ultrasonic energy so that the position of the nodes will shift over time so that a leak at a null or node will be detected. However, resort to this method adds complexity and expense to the testing hardware.

Ultrasonic transducers generally produce a low voltage output in response to received ultrasonic energy. Thus, it is necessary to amplify the detected signal using a high-gain preamplifier before it can be accurately processed. However, if low cost heterodyning and display circuitry are to be used, means must be made available to attenuate the amplified signal to prevent saturating these circuits when high input signals are present. This attenuation also adjusts the sensitivity of the device. For a hand-held unit, the degree of attenuation should be selectable by the user.

For example, U.S. Pat. No. 4,785,695 to Rose et al. discloses an ultrasonic leak detector with a variable resistor attenuator used to adjust the output level of an LED bar graph display. However, this attenuation method does not provide a way to establish fixed reference points to allow for repeatable measurements.

U.S. Pat. No. 5,089,997 to Pecukonis discloses an ultrasonic energy detector with an attenuation network positioned after an initial preamplifier and before the signal processing circuitry, which creates an audible output and an LED bar graph display. The resistors in the Pecukonis attenuation network are designed to provide an exponential relationship between the different levels of attenuation. However, Pecukonis does not heterodyne the detected signals to produce an audible output but rather teaches the benefits of a more complex set of circuits which compress a broad range of ultrasonic frequencies into a narrower audible range. For many applications, the cost and complexity of this type of circuitry is not necessary.

In addition to detecting ultrasonic sound escaping from a leak or defect, a detector using an acoustic transducer must be able to accurately locate the source that sound. To this end, conical sound collectors are used in conjunction with the transducer to increase its directionality as illustrated in U.S. Pat. No. 4,287,581 to Neale, Sr. However, conventional detectors do not utilize collection cones which are also specifically designed to provide additional input signal gain of an amount consistent with the units of measure provided by the detector.

When using ultrasonic energy to detect leaks, it is useful to have a portable ultrasonic sensor which indicates the presence and intensity of ultrasonic energy both visually and audibly. Goodman discloses an ultrasonic sensor which displays intensity of the detected signal on an output meter operable in either linear or logarithmic mode and also provides for audio output through headphones. U.S. Pat. No. 4,987,769 to Peacock et al. discloses an ultrasonic detector which displays the amplitude of the detected ultrasonic signal on a ten-stage logarithmic LED display. However, the detector disclosed in Peacock does not process the detected signal to produce an audible response, nor does it provide for signal attenuation after the initial pre-amplification stage.

SUMMARY OF THE INVENTION

The present invention is directed to providing a versatile, light weight, battery-operated, precision instrument for detecting ultrasound or vibration. The invention provides a wide dynamic range as well as fixed reference points through the entire range to provide for repeatable measurements. In one embodiment, the detector circuitry can be housed in a hand-held unit used to detect leaks. In another embodiment, the detector can be used with a grease gun to detect whether a sealed mechanical device such as a bearing, gear box, or transmission has been properly lubricated and if the device is faulty.

In an illustrative embodiment of the invention, the ultrasonic detector has an acoustic or contact ultrasonic transducer for detecting ultrasonic sound and converting it into an electric signal whose amplitude and frequency reflect that of the detected sound. A removable focusing probe funnels ultrasound into the transducer so as to collect the ultrasonic energy and focus it on a single transducer crystal. Prior art devices may use a plurality of transducers placed on a focusing surface. However, there are nulls in the reception with such an arrangement. Thus, the probe eliminates the possibility of missing a leak caused by receiving and/or positioning nulls that occur with multi-transducer receiving transducer modules. This probe also provides an additional 10 db of signal gain.

The output signal is passed through a high-gain preamp which has significant headroom so as to avoid saturation when large ultrasonic energy fields are detected. Further, the preamplifier is arranged as a charge amplifier so it will be relatively insensitive to changes in transducer output impedance or capacitance. The preamplifier's output is capacitively coupled to a logarithmic attenuator network in order to adjust for baseline or ambient noise levels and to prevent saturation of the output audio amplifier and display circuitry. The network provides fixed signal attenuation levels of 0 dB through −70 dB in −10 dB steps. A supplemental variable resistor is also provided to allow for additional attenuation when extremely high ultrasound intensity levels are present.

The attenuated signal is then fed into a heterodyning circuit where the ultrasonic frequency is shifted into the audible range, filtered and amplified. Heterodyning is achieved by commutating or multiplexing the inputs of a tuned audio frequency filter with a high frequency signal, then differentially filtering and amplifying the heterodyned audio output, which then drives the speaker output and bar graph display. This technique takes advantage of the differential inputs of the LM386 audio amplifier to provide additional carrier rejection as well as a doubled voltage swing.

The audio amplifier of the present invention provides a low impedance output so the heterodyned and amplified signal can be used to drive 8 or 16 ohm speakers or headphones at a fixed output level. This output may also be used as an input for signal processors or analyzers.

The audio amplifier also drives a logarithmic LED bar graph display. This display has ten bar segments calibrated at 3 dB per bar in order to provide an output display covering a 30 dB window. The use of the logarithmic attenuator in combination with the log output display converts the input signal to a decibel format. This combination also gives the detector a wide dynamic range of approximately 100 dB in 33⅓ fixed discrete steps. These steps provide a set of fixed, repeatable reference points anywhere within the display range of the instrument. An additional 10 dB of dynamic range can be obtained by removing the focusing probe if necessary.

In a second embodiment, the detector is attached to a lubrication tool such as a grease gun for use in detecting when a mechanical device has been properly lubricated. When dealing with sealed bearings, for example, there is normally no way to know when the proper amount of lubricant has reached the friction areas, such as the raceway and the ball bearings. Too much grease can build up the internal pressure in the bearing and cause damage or can "blow" the seal, allowing contaminants to get into the bearing. Too little grease can cause the bearings to overheat and seize due to excess friction. The same is true for other sealed mechanical devices such as gear boxes or transmissions.

Devices such as sealed bearings, gear boxes or transmissions generate ultrasonic energy when in use as a result of internal friction. As lubrication is applied, the internal friction is reduced. Consequently, the intensity of the generated ultrasound is lower. Measuring the level of ultrasound generated by the device as it is lubricated thus provides a way to determine when enough lubricant has been applied.

Additionally, devices such as sealed bearings generate higher than normal levels of ultrasound when they begin to fail. Because of the detector's fixed, repeatable reference points and wide dynamic range, the amount of ultrasound a specific lubricated bearing generates can be precisely measured and compared to a base line level. The degree to which the measured level exceeds normal indicates how badly the bearing has degraded.

Attaching the detector to a lubrication tool such as a grease gun has the further advantage of allowing the lubrication and ultrasound measurement procedures to be performed by one person, instead of the two required when conventional means are used.

BRIEF DESCRIPTION OF THE DRAWINGS

The foregoing and other features of the present invention will be more readily apparent from the following detailed description and drawings of illustrative embodiments of the invention in which:

FIG. 3A is an axial view of a removable ultrasonic focusing probe;

FIG. 3B is a lateral cross-sectional view of the focusing probe of FIG. 3A along line A–A';

FIG. 4A is an illustrative embodiment of the detector coupled with a grease gun;

FIG. 4B is a perspective view of the clip-on transducer housing; and

FIG. 4C is a view of the control panel of one embodiment of the detector illustrating the LED display and attenuation selection switch.

DETAILED DESCRIPTION OF THE PREFERRED EMBODIMENTS

Figure 1:
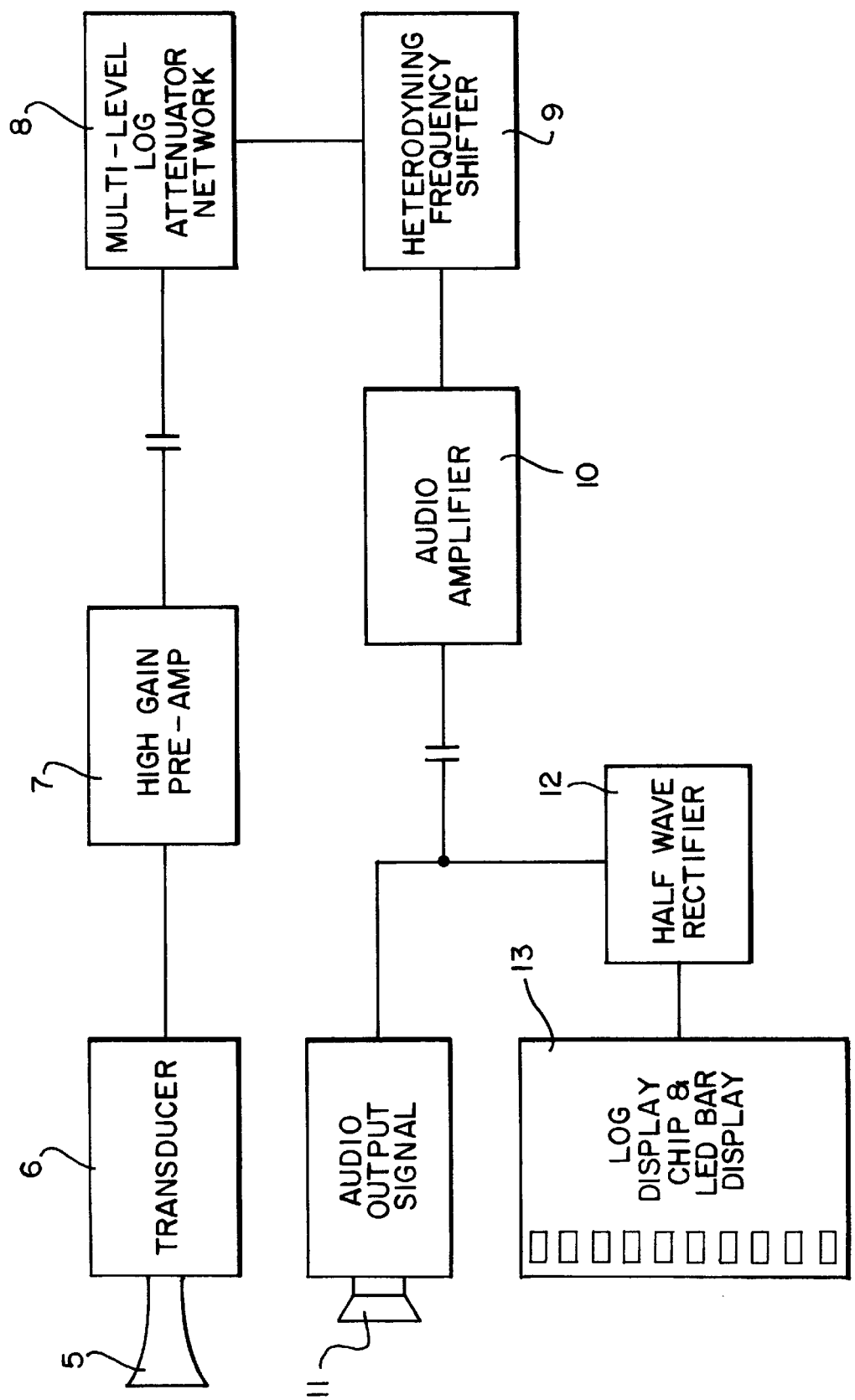
FIG. 1 is a block diagram of the present invention illustrating the arrangement of the circuit elements.

FIG. 1 shows a block diagram of one embodiment of the present invention. As illustrated in FIG. 1, ultrasonic energy is concentrated in the removable focusing probe 5 and applied to the ultrasonic transducer 6 to create an electronic signal whose amplitude and frequency represents that of the detected ultrasonic energy. Note that the transducer can be either an acoustic or a contact transducer, depending on the user's needs.

The output of the transducer 6 is fed into a high-gain preamp 7. The amplified input signal is then capacitively coupled to attenuator network 8 which attenuates the amplified input signal by one of several fixed logarithmic amounts according to the user's selection.

The attenuated signal is then fed into heterodyning frequency shifter 9 which generates an output signal of audible frequency and amplitude proportional to the ultrasonic frequency components of the applied signal. This output signal is amplified by audio amplifier 10 and supplied to low impedance output 11 where it can be used to drive speakers or headphones at a fixed output level and also may be used as an input for signal processors or analyzers. The amplified audio signal is also fed through a half-wave rectifier 12 then used to drive logarithmic display 13 which may be an LED bar graph display.

The individual circuit elements according to a preferred embodiment of the invention will now be described in more detail. All components used can have standard commercial temperature ranges and are off-the-shelf type items. The circuits are preferably driven from a battery with a voltage supply Vb ranging from 7.2 to 9 volts DC. The preferred embodiment may be constructed using a hybrid of surface mount and conventional thru hole components.

Figure 2A:
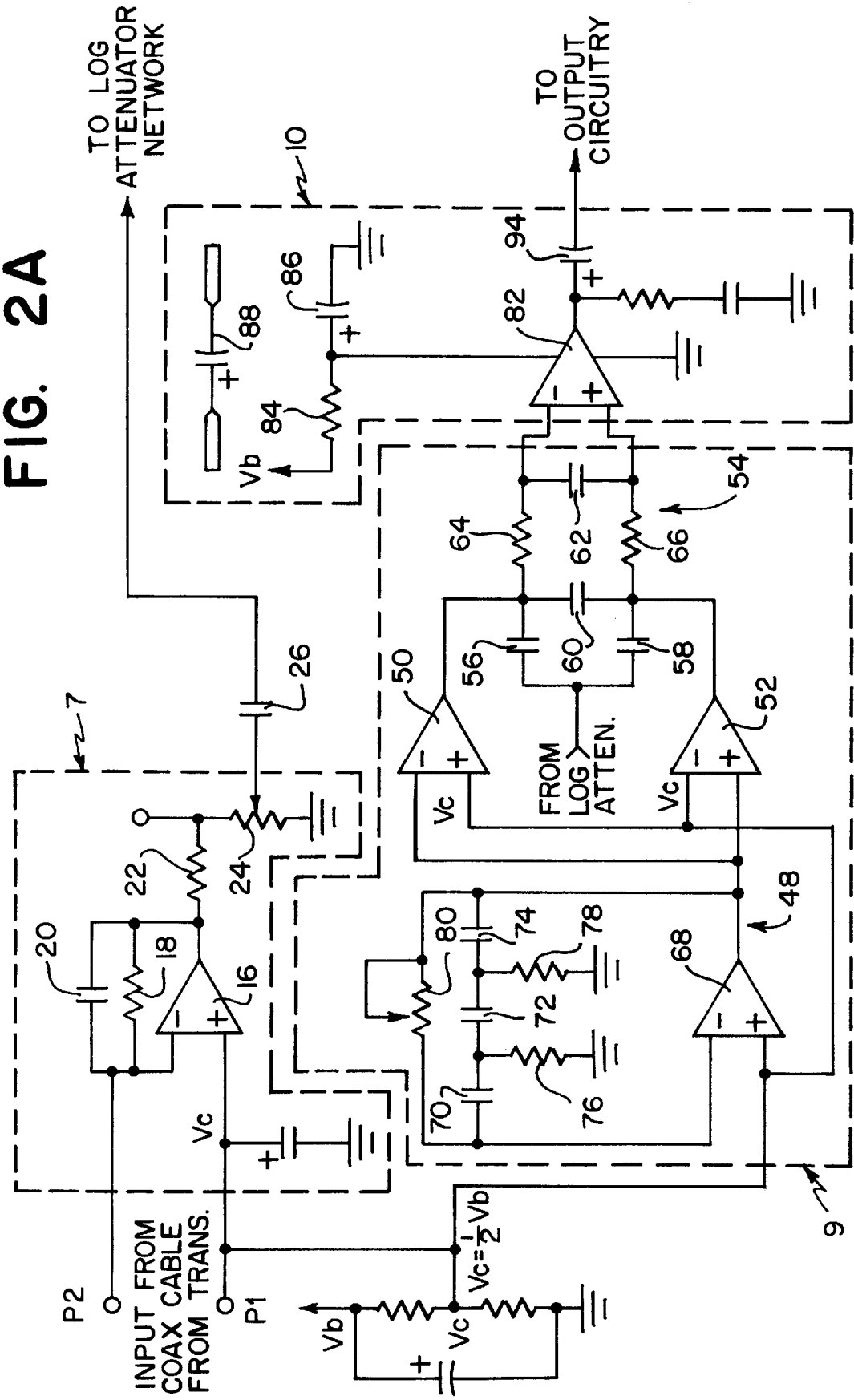
FIGS. 2A and 2B form a schematic diagram of a preferred embodiment of the present invention.

As seen in FIG. 2A, preamp 7 comprises an op-amp 16 with a parallel RC negative feedback loop comprising resistor 18 and capacitor 20. The non-inverting input of op amp 16 is biased to voltage Vc which is approximately half of supply voltage Vb from the battery. This amplifier configuration is classified as a charge amplifier because there is no series resistor between the transducers and the inverting input of the op amp 16. As a result, the signal from the transducers will send a charge in capacitor 20. The use of this type of amplifier makes the ultrasonic detector relatively insensitive to changes in transducer output impedance or capacitance. Also included as part of the output of preamp 7 is a supplemental attenuation circuit comprised of resistor 22 and variable resistor 24. Variable resistor 24 is normally set to provide no attenuation. Under extremely high ultrasound intensity levels, however, it can be adjusted to prevent the overdriving of the audio output to the speakers and display when the attenuator network 8 is set at maximum attenuation.

In the preferred embodiment, op amp 16 is a high gain IC amplifier such as an NE5532 chip. Resistor 18 is 1M ohm and capacitor 20 is 4 pF. This results in a preamplifier having a gain of about 600 v/v or 55 dB with a bandwidth of 20 KHz to 100 KHz and an amplitude of approximately 6 volts peak-to-peak. This provides a sufficiently large amount of headroom to avoid most saturation problems. Given the typical transducer output voltage level of 100 to 200 microvolts, it would require an input of 10 millivolts from the transducer to produce the 6 volt output level. This headroom also allows the attenuator to be placed after the preamp 7.

Figure 2B:
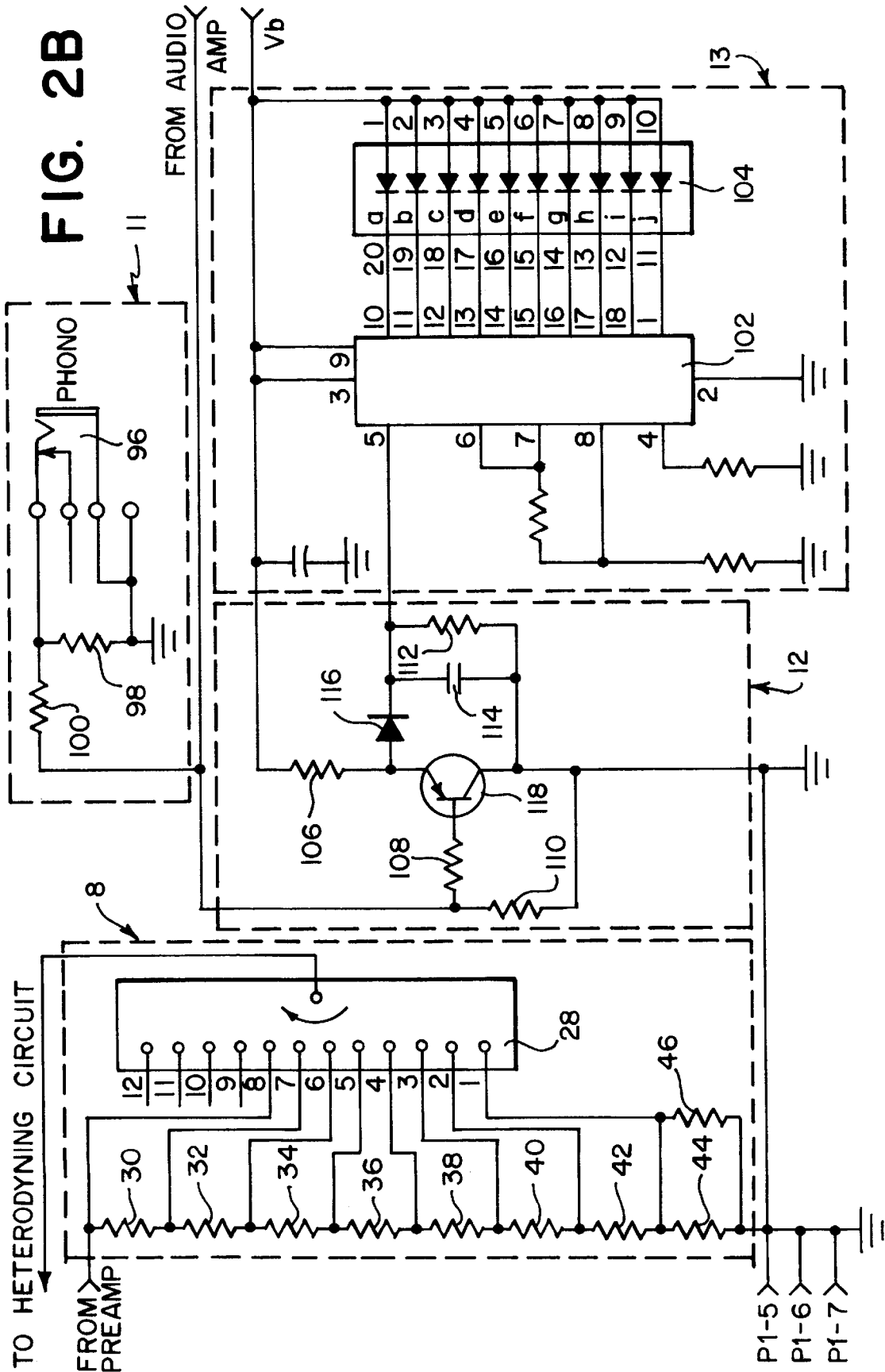

The output of preamp 7 is coupled through capacitor 26 to the log attenuator network 8 which is shown in FIG. 2B. Log attenuator network 8 comprises a multi-position switch 28 connected to series resistors 30, 32, 34, 36, 38, 40, 42, and 44. The values of the resistors are chosen to give the desired levels of attenuation, such as −10 dB per step. The amount of attenuation is a function of the ratios of resistance values and the interaction of the attenuator resistances and the input impedance of the heterodyning frequency shifter 9.

One method of determining the proper resistance values is to use a white noise source as an ultrasonic input signal. White noise is used because it characterizes ultrasonic leak and friction signals under turbulent flow conditions. The resistive values can then be adjusted while monitoring the output signal at different switch settings until the desired attenuation is achieved.

In the preferred embodiment, resistors 30, 32, 34, 36, 38, 40, and 42 are all of 1% tolerance and have values of 1.30K, 3.83K, 8.98K, 845, 140, 30.1, and 10 ohms respectively. Resistor 44 is 2.2 ohms with a 5% tolerance. In this configuration, the user can select between attenuation levels of from 0 dB to −70 dB in −10 dB intervals.

The attenuator network 8, like attenuator 24, is positioned after the high gain preamp 7 to prevent saturation of the audio output amplifier 10 and the overdriving of the output display 13. The output of the attenuation network is then fed to the heterodyning frequency shifter 9 and the audio amplifier 10 as shown in FIG. 2A.

The heterodyning frequency shifter 9 is comprised of a phase shift oscillator 48 which generates a commutating or switching signal, comparators 50 and 52, and tuned audio filter 54. The heterodyning circuit can be summarized as follows.

Phase shift oscillator 48 includes op amp 68 and an RC feedback network made up of capacitors 70, 72, 74, resistors 76, 78 and variable resistor 80. The non-inverting input of op amp 68 is biased to voltage Vc in the same fashion as op amp 16. Circuit components are chosen so the oscillator operates at a frequency of approximately 37.2 kHz with an output varying around voltage Vc.

In the preferred embodiment, op amp 68 is a high gain integrated circuit such as an NE5532 chip. Capacitors 70, 72, and 74 are 560 pF each. Resistors 76 and 78 are each 1K ohm and variable resistor 80 is 1M ohm.

The commutating signal from the output of op amp 68 is applied to the inverting input of comparator 50 and the non-inverting input of comparator 52. The non-inverting input of comparator 50 and the inverting input of comparator 52 are biased to voltage Vc. The comparators must have open collector outputs, such as are present in an LM339 IC chip.

The audio amplifier 10 comprises op amp 82, which can be an LM386 IC, and associated resistor 84, capacitors 86 and 88.

The tuned audio filter 54 includes capacitors 60 and 62, and resistors 64 and 66. In the preferred embodiment, capacitor 60 is 0.01 uF, capacitor 62 is 0.047 uF, and resistors 64 and 66 are both 1K ohm.

Heterodyning to shift the frequency of the detected ultrasonic signal into the audio range is achieved by commuting the inputs of the tuned audio frequency filter 54 at the high frequency of 37.2 kHz and then differentially filtering and applying the output to audio amplifier 10. The ultrasonic input signal is applied to the inputs of the tuned audio filter 54 through capacitors 56 and 58. On alternate half-cycles, the outputs of comparators 50 and 52 commutate the ultrasonic signal going to the differential inputs of op amp 82. Common mode rejection of op amp 82, combined with the filtering action of filter 54 extract the heterodyned audio which appears at the output of op amp 82. The extracted audio is coupled to the output circuitry through capacitor 94. In the described embodiment, the bandwidth of the heterodyning circuitry 9, 10 is approximately 0 to 20 kHz as compared to the bandwidth of 20 KHz to 100 kHz of the preamp circuit 7.

The output circuitry is depicted in FIG. 2B and comprises low impedance audio output 11 and a log LED display 13. The audio output 11 includes phono jack 96 and resistors 98 and 100. It is suitable for driving 8 or 16 ohm speakers or headphones at a fixed output level and is also suitable as an input for signal processors or analyzers.

In the preferred embodiment, the log display has a log response LED driver chip 102, such as the NSC 3915 log chip, which is used to drive a 10-segment LED bar display 104. The NSC 3915 is a proven low-cost device and is accurate and efficient for these purposes.

The log display circuitry 13 is driven by a half-wave rectifier 12 made up of resistors 106, 108, 110, and 112, capacitor 114, diode 116, and transistor 118. Rectifier 12 rectifies the heterodyned, log attenuated audio signal and feeds it to the log display chip 102 as an average value signal.

As can be seen, the use of the log attenuator in combination with the log output display converts the input signal to decibel display format. The 8 positions of the attenuator provide both a wide dynamic range and fixed reference points, i.e., each switch position provides fixed known amounts of attenuation. Variable potentiometers cannot provide this type of accuracy. For example, if two signals of very different amplitude are to be compared, the attenuator can be used to reduce the larger signal's amplitude range or increase the smaller's, and they then can be accurately measured or compared. The difference between the range of the larger and smaller signals' amplitude ranges will be known from the amount of attenuation needed, as evidenced by the switch position. The use of fixed reference points (used to determine base line or ambient noise levels) gives this sensor the flexibility to be used as a precision instrument and to provide repeatable measurements.

Additional accuracy and flexibility can be achieved through the use of a conical-shaped removable focusing probe 5 shown in FIGS. 3A and 3B. Use of probe 5 as a front end to the ultrasonic transducer 6 increases directivity and adds an additional 10 db through 12 dB of signal gain. The focusing probe 5 also funnels ultrasound into the single transducer 6. This funneling action reduces the chance that the user will miss a leak caused by receiving and/or positioning nulls that occur when using multi-transducer receiving transducer modules.

In an alternative embodiment, shown in FIG. 4A, the ultrasonic detector 206 can be connected to a lubrication tool such as grease gun 200 which has a neck 202 and a grease fitting adaptor 204. The ultrasonic circuitry is housed in casing 208 which is attached to the body of grease gun 200 by Velcro™ straps 212. Alternatively, casing 208 can be attached to grease gun 200 by clips, wire ties, or any other suitable means, such as welding and adhesives.

Ultrasonic transducer 6 (not shown) is contained within housing 210 and connected to the ultrasonic circuitry by wire 209. Transducer housing 210 attaches to grease gun 200 along neck 202 near grease fitting adaptor 204 or to adaptor 204 itself. One embodiment for transducer housing 210, a clip-on variety, is illustrated in FIG. 4B. Note, however, that transducer 6 can be attached by any other mechanism that places it in acoustical contact with grease fitting adaptor 204 or neck 202. Other ways to attach the transducer to the grease gun include by a strap or magnetically. Alternatively, neck 202 or grease fitting adaptor 204 can be specially constructed with means to securely receive a suitably shaped housing 210.

When a mechanical device is in use, internal friction results in the generation of ultrasound. As lubrication is applied and reaches the friction or ultrasound generating surfaces, the intensity of the generated ultrasound is reduced. Coupling an ultrasonic detector with a lubrication tool such as a grease gun allows a single user to apply lubrication to a mechanical device while simultaneously monitoring the intensity of ultrasonic energy generated by that device. This allows the user to see when the detected ultrasonic energy drops to its lowest level, and thus when enough lubrication has been applied.

In one use for this embodiment, grease gun 200 can be used to lubricate sealed bearing 220. Because bearing 220 is sealed, there is normally no way to know when the proper amount of grease has reached the friction areas, such as the raceway and the ball bearings. Too much grease can build up the internal pressure of the bearing and cause damage or can "blow" the seal, allowing contaminants to get into the bearing. Too little grease can cause the bearings to overheat and seize due to excess friction. A similar problem occurs when lubricating other sealed mechanical devices such as gear boxes or transmissions.

In use, grease fitting adaptor 204 attaches to grease fitting 214 on bearing 220. Grease fitting adaptor 204 then acts as a wave guide, transmitting the ultrasound generated by sealed bearing 220 to transducer 6. As lubricant is applied, the level of ultrasound generated by bearing 220 is indicated visually on LED bar display 104 and audibly through headphones (not shown) connected to phono jack 96. See FIG. 4C. As shown in FIG. 4C, using the fixed attenuation setpoints selectable by attenuator switch 28 and by monitoring LED bar graph display 104 on the control panel of the unit, the drop in the level of detected ultrasonic energy can be precisely measured.

Lubrication is packed into bearing 220 until the detected level of ultrasound reaches its lowest level, an indication that enough lubricant has been applied. Since the detector can precisely measure the differences in amplitude of the ultrasonic signal, the user has the ability to prevent the bearing from being "over packed" and consequently blowing out the seal.

This embodiment can also be used to detect faulty bearings. In use, good bearings generate a normal base level of ultrasonic energy. When measured, this energy level corresponds to a specific position of the log attenuator switch 28 and a certain number of lit bars on LED display 104. This level can be determined, for example, by attaching grease gun 200 to a properly lubricated bearing known to be in good condition, and then measuring the detected ultrasound. The fixed reference points ensure that this measurement is repeatable and allow the value to be used as a reference or baseline when subsequent measurements are made.

In practice, an operator attaches grease fitting adapter 204 of grease gun 200 to grease fitting 214 on bearing 220 and then measures the intensity of emitted ultrasound. If the detected level is higher than the predetermined base level, lubrication can be applied until the detected ultrasound level reaches its lowest level. However, even after a faulty bearing is lubricated, it will still produce a higher level of ultrasound than normal. The number of decibels above the base line reading indicates the stage of failure the bearing is in.

A reading of 8 dB above baseline indicates that the bearing is in a pre-failure stage, the earliest stage of failure. In this stage, the bearing may have developed flaws not visible to the human eye, such as hairline cracks or microscopic spalls. Because of the fixed reference points and the 3 dB per bar scale of the LED bar display, even this small increase in generated ultrasonic energy can be accurately detected.

A reading of 16 dB above baseline indicates that the bearing is at failure stage. At this level, the bearing should be replaced or frequently monitored. When the detected level of ultrasound is 35–50 dB above normal, the bearing is at a catastrophic stage and rapid failure is imminent. This is a highly dangerous condition since the bearing clearances increase and cause additional friction and rubbing within a machine, thus causing potential damage to other components.

Note that while the prior discussion addressed using one embodiment of the invention to lubricate and test a sealed bearing, this embodiment can also be used with other sealed mechanical devices such as gear boxes and transmissions for the same purposes.

While the invention has been particularly shown and described with reference to preferred embodiments thereof, it will be understood by those skilled in the art that various changes in form and details may be made therein without departing from the spirit and scope of the invention.

What is claimed is:

1. An ultrasonic detector comprising:
   an ultrasonic transducer which produces an electrical output signal in the ultrasonic frequency range which is related to the intensity and frequency of received ultrasonic energy;

a high gain charge preamplifier connected to said transducer and generating an amplified version of the transducer electrical output signal;

a multi-level logarithmic attenuator receiving the output of the preamplifier and creating an attenuated version of the output signal of said preamplifier with at least one fixed reference point;

a variable attenuator with an input connected to the output of the preamplifier and an output connected to the logarithmic attenuator, said variable attenuator including a fixed resistor connected to the input of the variable attenuator, a potentiometer connected between the resistor and a reference level, the wiper of the potentiometer being connected to the output of the variable attenuator;

a frequency shift circuit connected to receive the output of the logarithmic attenuator and producing an audio frequency range signal related in magnitude and frequency to the attenuated signal, but shifted from the ultrasonic frequency range to an audio frequency range;

an audio amplifier which receives the audio signal from the frequency shift circuit and amplifies the audio signal to create an amplified audio output signal; and a signal level indicator receiving the amplified audio output signal and providing an indication of the magnitude of the amplified audio output signal of the audio amplifier.

2. An ultrasonic detector as claimed in claim 1 wherein said charge preamplifier comprises:

an operational amplifier having an output, an inverting input and a non-inverting input, a resistor and capacitor connected in parallel between the output and inverting input of the operational amplifier, said transducer being directly connected between the inverting and non-inverting inputs of said operational amplifier.

3. An ultrasonic detector as claimed in claim 1 wherein said logarithmic attenuator has seven steps of 10 dB per step.

4. An ultrasonic detector as claimed in claim 3 wherein said logarithmic attenuator comprises:

eight resistances connected in series between the logarithmic attenuator input and a reference level, and a multi-position switch with inputs connected to the logarithmic attenuator input and the junction of the resistances respectively, the wiper of the switch being connected to the output of the logarithmic attenuator, the values of the resistances being such that the output of the logarithmic attenuator is related to the preamplifier output and logarithmic attenuations thereof in seven fixed 10 dB steps.

5. An ultrasonic detector as claimed in claim 1 wherein said frequency shift circuit comprises:

an oscillator which generates a switching signal;

first and second comparators each having inverting and non-inverting inputs, the switching signal being applied to the inverting input of said first comparator and the non-inverting input of said second comparator and a reference voltage being applied to the non-inverting input of said first comparator and the inverting input of said second comparator; and a balanced audio frequency filter with two signal inputs, two comparator inputs and two outputs, the output of the logarithmic attenuator being applied to both filter signal inputs, the outputs of the comparators being applied to respective filter comparator inputs and the filter outputs being applied to the audio amplifier.

6. An ultrasonic detector as claimed in claim 5 wherein said balanced audio frequency filter comprises:

first and second input capacitances connected between the signal inputs and the comparator inputs respectively, a third capacitance connected between the comparator inputs;

first and second resistances connected between the comparator inputs and the outputs respectively; and a fourth capacitance connected between the outputs.

7. An ultrasonic detector as claimed in claim 1 wherein said frequency shift circuit has a balanced output and said audio amplifier comprises an operational amplifier with inverting and non-inverting inputs to which the balanced output is connected and having high common mode rejection.

8. An ultrasonic detector as claimed in claim 1 wherein said signal level indicator comprises a speaker which receives the output of the audio amplifier.

9. An ultrasonic detector as claimed in claim 1 wherein said signal level indicator comprises:

a rectifier circuit for rectifying the output of said audio amplifier to provide a rectified signal;

a logarithmic display circuit driven by the rectified signal to provide an LED bar display signal; and an LED bar display driven by the bar display signal so that the number of bars of the display which are illuminated relate to the strength of the detected ultrasonic energy in decibels.

10. An ultrasonic detector as claimed in claim 1 further including a removable focusing probe for receiving the ultrasonic energy and funneling the ultrasonic energy to the transducer.

11. The removable focusing probe of claim 10 wherein said probe is conical and provides approximately 10 dB of signal gain when engaged.

12. A method of detecting ultrasonic energy comprising the steps of:

converting the ultrasonic energy into an electrical signal related to the intensity and frequency of the ultrasonic energy;

amplifying said electrical signal with a high gain preamplifier;

converting said amplified signal into an audio frequency signal related in magnitude and frequency to the attenuated signal by:

a. commutating a high frequency switching signal with said preamplified signal to produce a pair of commutated signals;

b. differentially filtering said commutated signals with a balanced audio frequency filter to provide a pair of balanced filter signals; and c. amplifying the balanced filtered signals in an audio amplifier having high common mode rejection to produce an audio frequency signal; and indicating the magnitude of the amplified audio frequency signal.

13. The method of detecting ultrasonic energy as claimed in claim 12 further including the step of producing said high frequency switching signal with a phase shift oscillator.

14. The method of detecting ultrasonic energy as claimed in claim 12 wherein said balanced audio filter comprises first and second inputs and an output, and wherein said high frequency switching signal is commutated with said preamplified signal by the steps of:

applying said high frequency switching signal to the inverting input of a first comparator and the non-inverting input of a second comparator;

applying the output of said first comparator to said first audio filter input and the output of said second comparator to said second audio filter input;

capacitively coupling said preamplified signal to said first filter input and capacitively coupling said preamplified signal to said second filter input; and applying said filter output to said audio amplifier.

15. The method of detecting ultrasonic energy as claimed in claim 12 with the additional step of applying said audio amplified signal to a speaker.

16. The method of detecting ultrasonic energy as claimed in claim 12 further including the steps of:

logarithmically attenuating said preamplified signal with at least one fixed reference point before the step of converting said attenuated signal into an audio frequency signal; and indicating the magnitude of said audio amplified signal by applying said audio amplified signal to a logarithmically scaled LED bar graph display.

17. A frequency shift circuit for use in an ultrasonic detector which receives an electrical signal in the ultrasonic frequency range related to the intensity and frequency of ultrasonic energy received by an ultrasonic transducer and produces an audio frequency range signal related in magnitude and frequency to the received ultrasonic frequency range signal but shifted to an audio frequency range, said frequency shift circuit comprising:

an oscillator which generates a switching signal;

first and second comparators each having inverting and non-inverting inputs, said switching signal being applied to the inverting input of said first comparator and the non-inverting input of said second comparator and a reference voltage being applied to the non-inverting input of said first comparator and the inverting input of said second comparator; and a balanced audio frequency filter with two signal inputs, two comparator inputs and an output, the received ultrasonic frequency range signal being applied to both filter signal inputs and the comparator outputs being applied to respective filter comparator inputs, said balanced audio frequency filter providing said audio frequency range signal in said filter output.

18. The frequency shift circuit of claim 17 wherein the output of said balanced audio frequency filter comprises two filter output signals and said filter comprises:

first and second input capacitances connected between respective filter signal inputs and filter comparator inputs, a third capacitance connected between the filter comparator inputs;

first and second resistances connected between respective filter comparator inputs and filter outputs; and a fourth capacitance connected between the filter output signals.

19. The frequency shift circuit of claim 17, further comprising an audio amplifier which receives and amplifies said audio frequency range signal to create an amplified audio output signal.

20. The frequency shift circuit of claim 19, wherein said filter output comprises a pair of balanced signals and said audio amplifier comprises an operational amplifier with high common mode rejection and having inverting and non-inverting inputs to which the filter output is connected.

21. The frequency shift circuit of claim 17, further comprising a multi-level logarithmic attenuator which attenuates the ultrasonic frequency range signal before it is received by said frequency shift circuit.

22. The frequency shift circuit of claim 17, further comprising a preamplifier which amplifies the ultrasonic frequency range signal before it is received by said frequency shift circuit.

23. The frequency shift circuit of claim 22, wherein said preamplifier comprises:

an operational amplifier having an output, an inverting input and a non-inverting input;

a resistor and capacitor connected in parallel between the output and inverting input of the operational amplifier, said transducer being directly connected between the inverting and non-inverting inputs of said operational amplifier.

24. An ultrasonic detector comprising:

an ultrasonic transducer which produces an electrical output signal in the ultrasonic frequency range which is related to the intensity and frequency of received ultrasonic energy;

a logarithmic attenuator having a plurality of substantially equal logarithmic attenuation steps, said attenuator receiving said ultrasonic frequency range signal and creating an attenuated signal;

a selectively operable focusing probe that receives said ultrasonic energy and funnels it to the transducer, wherein said probe provides a signal gain magnitude substantially corresponding to the level of attenuation of one or more of said logarithmic attenuation steps; and a logarithmic signal level indicator receiving the attenuated signal and providing an indication of the magnitude of the attenuated signal.

25. The ultrasonic detector of claim 24 further comprising:

a frequency shift circuit receiving the output of said logarithmic attenuator and producing an audio frequency range signal related in magnitude and frequency to the attenuated signal, but shifted from the ultrasonic frequency range to an audio frequency range; and an audio amplifier connected between said frequency shift circuit and said signal level indicator which receives and amplifies the audio frequency range signal from the frequency shift circuit to create an amplified audio output signal.

26. The ultrasonic detector as claimed in claim 25, wherein said signal level indicator comprises a speaker which receives the output of the audio amplifier.

27. The ultrasonic detector as claimed in claim 25, wherein said signal level indicator comprises:

a rectifier circuit for rectifying the output of said audio amplifier to provide a rectified signal;

a logarithmic display circuit driven by the rectified signal to provide an LED bar display signal; and an LED bar display driven by the bar display signal so that the number of bars of the display which are illuminated relate to the strength of the detected ultrasonic energy in decibels.

28. The ultrasonic detector of claim 24, wherein said attenuation steps are approximately 10 dB per step and said focusing probe provides approximately 10 dB of signal gain when operated.

29. The ultrasonic detector as claimed in claim 24, wherein said logarithmic attenuator comprises:

a plurality of resistances connected in series between the logarithmic attenuator input and a reference voltage level, and a multi-position switch having an output selectably connected to a junction of one of said series resistances, the values of the resistances being such that successive junctions of the series resistances present logarithmic attenuations of said preamplifier output in substantially fixed 10 dB steps.

30. An ultrasonic detector comprising:

an ultrasonic transducer which produces an electrical output signal in the ultrasonic frequency range which is related to the intensity and frequency of received ultrasonic energy;

a preamplifier connected to said transducer and generating an amplified version of the transducer electrical output signal;

a frequency shift circuit receiving the output of the preamplifier and producing an audio frequency range signal related in magnitude and frequency to the received preamplified signal but shifted from the ultrasonic frequency range to an audio frequency range, said frequency shift circuit comprising:

an oscillator which generates a switching signal;

first and second comparators each having inverting and non-inverting inputs, said switching signal being applied to the inverting input of said first comparator and the non-inverting input of said second comparator and a reference voltage being applied to the non-inverting input of said first comparator and the inverting input of said second comparator; and a balanced audio frequency filter with two signal inputs, two switched signal inputs and a filter output, the received preamplified signal being applied to said filter signal inputs and the outputs of said comparators being applied to respective switched signal inputs;

an audio amplifier which receives an audio frequency signal from the filter output of said frequency shift circuit and amplifies the audio frequency signal to create an amplified audio output signal; and a signal level indicator receiving the amplified audio output signal and providing an indication of the magnitude of the amplified audio output signal of the audio amplifier.

31. The ultrasonic detector as claimed in claim 30 wherein the output of said balanced audio frequency filter comprises two filter output signals and said filter comprises:

first and second input capacitances connected between respective filter signal inputs and filter comparator inputs, a third capacitance connected between the filter comparator inputs;

first and second resistances connected between respective filter comparator inputs and filter outputs; and a fourth capacitance connected between said filter output signals.

32. The ultrasonic detector as claimed in claim 30, wherein said filter output comprises a pair of balanced signals and said audio amplifier comprises an operational amplifier with inverting and non-inverting inputs to which the filter output signals are connected.

33. The ultrasonic detector of claim 30, further comprising a multi-level logarithmic attenuator with at least one fixed reference point and which attenuates the preamplified signal before it is received by said frequency shift circuit.

34. The ultrasonic detector as claimed in claim 30 wherein said charge preamplifier comprises:

an operational amplifier having an output, an inverting input and a non-inverting input;

a resistor and capacitor connected in parallel between the output and inverting input of the operational amplifier, said transducer being directly connected between the inverting and non-inverting inputs of said operational amplifier.

35. An ultrasonic detector comprising:

an ultrasonic transducer which produces an electrical output signal in the ultrasonic frequency range which is related to the intensity and frequency of received ultrasonic energy;

a high gain charge preamplifier connected to said transducer and generating an amplified version of the transducer electrical output signal;

a multi-level logarithmic attenuator receiving the output of the preamplifier and creating an attenuated version of the output signal of said preamplifier, said logarithmic attenuator comprising:

eight resistances connected in series between the logarithmic attenuator input and a reference level, and a multi-position switch with inputs connected to the logarithmic attenuator input and the junction of the resistances respectively, the wiper of the switch being connected to the output of the logarithmic attenuator, the values of the resistances being such that the output of the logarithmic attenuator is related to the preamplifier output and logarithmic attenuations thereof in seven fixed 10 dB steps;

a frequency shift circuit connected to receive the output of the logarithmic attenuator and producing an audio frequency range signal related in magnitude and frequency to the attenuated signal, but shifted from the ultrasonic frequency range to an audio frequency range;

an audio amplifier which receives the audio signal from the frequency shift circuit and amplifies the audio signal to create an amplified audio output signal; and a signal level indicator receiving the amplified audio output signal and providing an indication of the magnitude of the amplified audio output signal of the audio amplifier.

36. An ultrasonic detector as claimed in claim 35, wherein said signal level indicator comprises a speaker which receives the output of the audio amplifier.

37. An ultrasonic detector as claimed in claim 35, wherein said signal level indicator comprises:

a rectifier circuit for rectifying the output of said audio amplifier to provide a rectified signal;

a logarithmic display circuit driven by the rectified signal to provide an LED bar display signal; and an LED bar display driven by the bar display signal so that the number of bars of the display which are illuminated relate to the strength of the detected ultrasonic energy in decibels.

38. An ultrasonic detector as claimed in claim 35 further including a removable focusing probe for receiving the ultrasonic energy and funneling the ultrasonic energy to the transducer.

* * * * *